US008058235B1

United States Patent
Coleman et al.

(10) Patent No.: US 8,058,235 B1
(45) Date of Patent: *Nov. 15, 2011

(54) WATER-MEDIATED CONTROL OF DEPOLYMERIZATION STEP OF GLATIRAMER ACETATE SYNTHESIS

(75) Inventors: Claire Coleman, Pelham, NH (US); John Schaeck, Somerville, MA (US); Alicia Thompson, Danvers, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/187,243

(22) Filed: Jul. 20, 2011

Related U.S. Application Data

(63) Continuation of application No. 12/754,344, filed on Apr. 5, 2010.

(60) Provisional application No. 61/166,608, filed on Apr. 3, 2009, provisional application No. 61/247,321, filed on Sep. 30, 2009.

(51) Int. Cl.
*A61K 38/16* (2006.01)
*C07K 1/02* (2006.01)

(52) U.S. Cl. ............ 514/2; 514/12; 528/312; 528/314; 528/315; 528/318; 528/325; 530/300; 530/324; 530/333; 530/335; 530/336; 530/337; 530/344; 530/402

(58) Field of Classification Search .................. 514/1.1, 514/12; 528/312, 314, 315, 318, 325; 530/300, 530/324, 333, 335, 336, 337, 344, 402
See application file for complete search history.

(56) References Cited

U.S. PATENT DOCUMENTS

| | | | |
|---|---|---|---|
| 3,849,550 A * | 11/1974 | Teitelbaum et al. | ............ 4/78.29 |
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,342,476 B1 | 1/2002 | Konfino et al. | |
| 6,362,161 B1 | 3/2002 | Konfino et al. | |
| 6,620,847 B2 | 9/2003 | Konfino et al. | |
| 7,049,399 B2 | 5/2006 | Bejan et al. | |
| 7,199,098 B2 | 4/2007 | Konfino et al. | |
| 7,495,072 B2 | 2/2009 | Dolitzky | |
| 7,884,187 B2 | 2/2011 | Zhu et al. | |
| 2006/0154862 A1* | 7/2006 | Ray et al. | ........................ 514/12 |
| 2006/0172942 A1 | 8/2006 | Dolitzky | |
| 2007/0021324 A1 | 1/2007 | Dolitzky | |
| 2007/0141663 A1 | 6/2007 | Ding et al. | |
| 2009/0035816 A1 | 2/2009 | Chan et al. | |
| 2009/0263347 A1* | 10/2009 | Jiang et al. | ................. 424/78.37 |
| 2010/0036092 A1 | 2/2010 | Hsiao et al. | |
| 2010/0234566 A1 | 9/2010 | Ray et al. | |
| 2010/0256039 A1* | 10/2010 | Coleman et al. | ............... 514/1.1 |
| 2010/0324265 A1 | 12/2010 | Kota et al. | |

FOREIGN PATENT DOCUMENTS

| | | |
|---|---|---|
| EP | 1807467 | 8/2009 |
| JP | 2004/140039 | 5/2004 |
| JP | 2008/016838 | 1/2008 |
| KR | 100695500 B1 | 3/2007 |
| KR | 1020080001881 A | 1/2008 |
| WO | WO95/31990 | 11/1995 |
| WO | WO96/32119 | 10/1996 |
| WO | WO2006/029393 | 3/2006 |
| WO | WO2006/050122 | 11/2006 |
| WO | WO2007/022193 | 2/2007 |
| WO | WO2009/129018 | 10/2009 |
| WO | WO2010/017292 | 11/2010 |
| WO | WO2010/140157 | 12/2010 |

OTHER PUBLICATIONS

Blanchette et al., "Glatiramer acetate: evidence for a dual mechanism of action," J Neurol (2008) 255(Supp 1):26-36.
Deming, Timothy J., "Synthetic polypeptides for biomedical applications," Progress in Polymer Science (Aug.-Sep. 2007) 32(8-9):858-875.
Hirschmann et al., "Controlled synthesis of peptides in aqueous medium. VIII. Preparation and use of novel .alpha.-amino acid N-carboxyanhydrides," J Am Chem Soc (1971) 93(11):2746-2754.
Holladay J E et al. "Catalytic Hydrogenation of Glutamic Acid" Applied Biochemistry and Biotechnology, 113-116:pp. 857-869 (2004).
Schechter et al., "Synthetic antigens with sequential and conformation-dependent determinants containing the same L-tyrosyl-L-alanyl-L-glutamyl sequence," Eur J Biochem (1971) 20:309-320.
Sela et al., "Studies on the chemical basis of the antigenicity of proteins, 5. Synthesis, characterization and immunogenicity of some multichain and linear polypeptides containing tyrosine," Biochem J (1962) 85:223-235.
Sorup et al., "Physicochemical studies of a branched polypeptide antigen: poly(1-Tyr,1-Glu)-poly(dl-Ala)—poly(1-Lys)," Biochimica et Biophysica Acta (BBA)—Protein Structure (Sep. 27, 1977) 494(1):9-18.
Teitelbaum et al., "Copaxone," Comprehensive Medicinal Chemistry II (2007) 8:173-185.
Material Safety Data Sheet for Hydrobromic Acid 33-35%, in Acetic Acid; http://fscimage.fishersci.com/msds/40066.htm; retrieved Apr. 13, 2011.
Aventis Pharmaceuticals, Inc., National Drug Code (NDC) 0088-1153-30 (Copaxone®) Label, Version 1 (published Jul. 25, 2006).

* cited by examiner

*Primary Examiner* — Cecilia J Tsang
*Assistant Examiner* — Thang K Chiu
(74) *Attorney, Agent, or Firm* — Fish & Richardson P.C.

(57) ABSTRACT

Methods of making copolymers are described.

20 Claims, 2 Drawing Sheets

WATER-MEDIATED CONTROL OF DEPOLYMERIZATION STEP OF GLATIRAMER ACETATE SYNTHESIS

RELATED APPLICATION INFORMATION

This application is a continuation and claims priority to U.S. application Ser. No. 12/754,344, filed on Apr. 5, 2010, and claims priority to U.S. Provisional Application Ser. No. 61/166,608, filed on Apr. 3, 2009 and U.S. Provisional Application Ser. No. 61/247,321, filed on Sep. 30, 2009, all of which are hereby incorporated by reference.

BACKGROUND

Glatiramer acetate (also known as copolymer-1 and marketed as the active ingredient in COPAXONE® by Teva Pharmaceutical Industries Ltd., Israel) is used in the treatment of the relapsing-remitting form of multiple sclerosis (RRMS). According to the COPAXONE® product label, glatiramer acetate (GA) consists of the acetate salts of synthetic polypeptides containing four naturally occurring amino acids: L-glutamic acid, L-alanine, L-tyrosine, and L-lysine with a reported average molar fraction of 0.141, 0.427, 0.095, and 0.338, respectively. Chemically, glatiramer acetate is designated L-glutamic acid polymer with L-alanine, L-lysine and L-tyrosine, acetate (salt). Its structural formula is:

$(Glu, Ala, Lys, Tyr)_x \cdot xCH_3COOH$
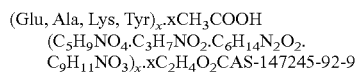
$(C_9H_{11}NO_3)_x \cdot xC_2H_4O_2$ CAS-147245-92-9

SUMMARY OF THE INVENTION

The invention is based, at least in part, on the identification of methods for controlling the level of L-pyroGlutamic Acid (pyro-Glu) in glatiramer acetate (GA). Pyro-Glu is present in GA, and the ability to control the level of pyro-Glu in GA is useful in controlling both product and process quality in the manufacture of GA.

Described herein is a method for preparing a composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer (Intermediate-1); treating the protected copolymer to partially depolymerize the protected copolymer and deprotect benzyl protected groups thereby generating a partially depolymerized, benzyl-deprotected product (Intermediate-2); treating the partially depolymerized product to deprotect TFA-protected lysines thereby generating a TFA-deprotected product (Intermediate-3) and further processing the Intermediate-3 to create glatiramer acetate, wherein the improvement comprises: having water present during at least a portion of the depolymerization step.

Also described herein is a method for preparing a composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer (Intermediate-1); treating the protected copolymer to partially depolymerize the protected copolymer and deprotect benzyl protected groups thereby generating a partially depolymerized, benzyl-deprotected product (Intermediate-2); and treating the partially depolymerized product to deprotect TFA-protected lysines thereby generating a TFA-deprotected product (Intermediate-3); and further processing the Intermediate-3 to create glatiramer acetate, wherein the improvement comprises: adjusting the water present during at least a portion of the depolymerization step so that amount water is present during at least a portion of the depolymerization step is within a predetermined range.

Also described herein is a method for preparing a composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer (Intermediate-1); treating the protected copolymer to partially depolymerize the protected copolymer and deprotect benzyl protected groups thereby generating a partially depolymerized, benzyl-deprotected product (Intermediate-2); treating the partially depolymerized, benzyl-deprotected product to deprotect TFA-protected lysines thereby generating acetate TFA-deprotected product (Intermediate-3); and further processing Intermediate-3 to create glatiramer acetate, wherein the improvement comprises: controlling the water present during at least a portion of the depolymerization step so that amount water is present during at least a portion of the depolymerization step is within a predetermined range.

In various embodiments of the forgoing methods: water is present, adjusted or controlled at the beginning of the depolymerization step; water is added during the depolymerization step; the water present during the depolymerization step is present within a predetermined range (e.g., the predetermined range is 4-25%, 5-25%, 4-20%, 4-16%, 7-15%, 8-14%, 9-13%, 10-12%, 13-19%, 14-18% w/w against Intermediate-1); the depolymerization proceeds for 16-64 hrs, preferably at least 25 hrs (e.g., 25-55 hrs, at least 30 hrs, 30-50 hrs, at least 40 hrs, 43-47 hrs); the depolymerization reaction is carried out at 17-35° C., e.g., 18-30° C., 18-22° C.; the depolymerization step comprises contacting the protected copolymer with a solution comprising phenol, HBr and acetic acid; the concentration of pyroglu in the purified glatiramer acetate is 2000-7000 ppm (e.g., 2500-6000 ppm; 2500-5500 ppm; 3000-5000 ppm; 3500-4500 ppm, 2400-6500 ppm); the Mp of the purified glatiramer acetate is 5,000-9,000 Da (e.g., 6,500-7,500 Da); in one embodiment water is present during the depolymerization step at 11.2% w/w against Intermediate-1, the depolymerization proceeds for 43-47 hrs at 18-22° C. and the process produces purified glatiramer acetate in which pyro-Glu is present at 0.24-0.65 w/w (2400-6500 ppm). The improvement further comprises: preparing a pharmaceutical composition comprising at least a portion of the purified glatiramer acetate; and in some cases the method further includes measuring the amount of water in the depolymerization step at least once.

Also described is a method for preparing a composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups thereby generating a partially depolymerized product; treating the partially depolymerized product to deprotect TFA-protected lysines thereby generating a TFA-deprotected product; and processing the TFA-deprotected product to create glatiramer acetate, wherein water is present during at least a portion of the depolymerization step.

An additional method is a method for preparing a composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups thereby generating a partially depolymerized product; treating the partially depolymerized product to deprotect TFA-protected lysines thereby generating glatiramer acetate; and purifying the glatiramer acetate to create purified glatiramer acetate, wherein water is present during at least a portion of the depolymerization step within a predetermined range.

An additional described method is a method for preparing a composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups thereby generating a partially depolymerized product; treating the partially depolymerized product to deprotect TFA-protected lysines thereby generating a TFA-deprotected product; and processing the a TFA-deprotected product to create glatiramer acetate, wherein the water present during at least a portion of the depolymerization step is controlled to be within a predetermined range.

In various embodiments of the foregoing methods: water is present, adjusted or controlled at the beginning of the depolymerization step; water is added during the depolymerization step; the water present during the depolymerization step is present within a predetermined range (e.g., the predetermined range is 4-25%, 5-25%, 13-19%, 14-18% w/w against Intermediate-1); the depolymerization proceeds for at least 25 hrs (e.g., at least 30 hrs or at least 40 hrs); the depolymerization step comprises contacting the protected copolymer with a solution comprising phenol, HBr and acetic acid; the concentration of pyroglu in the purified glatiramer acetate is 2000-7000 ppm (e.g., 2500-6000 ppm; 2500-5500 ppm; 3000-5000 ppm; 3500-4500 ppm, 2400-6500 ppm (0.24%-0.65% w/w); the Mp of the purified glatiramer acetate is 5,000-9,000 Da (e.g., 6,500-7,500 Da); the improvement further comprises: preparing a pharmaceutical composition comprising at least a portion of the purified glatiramer acetate; the step of treating the partially depolymerized product to deprotect TFA-protected lysines comprises treating the depolymerized product with piperidine; the protected copolymer is isolated and at least partially dried prior to treating the protected copolymer to partially depolymerize the protected copolymer and deprotect benzyl protected groups; the partially depolymerized product is isolated and at least partially dried prior to the step of treating the partially depolymerized product to deprotect TFA-protected lysines; in some cases the method further includes measuring the amount of water in the depolymerization step at least once.

As used herein, a "copolymer", "amino acid copolymer" or "amino acid copolymer preparation" is a heterogeneous mixture of polypeptides comprising a defined plurality of different amino acids (typically between 2-10, e.g., between 3-6, different amino acids). A copolymer may be prepared from the polymerization of individual amino acids. The term "amino acid" is not limited to naturally occurring amino acids, but can include amino acid derivatives and/or amino acid analogs. For example, in an amino acid copolymer comprising tyrosine amino acids, one or more of the amino acids can be a homotyrosine. Further, an amino acid copolymer having one or more non-peptide or peptidomimetic bonds between two adjacent residues is included within this definition.

DETAILED DESCRIPTION OF THE INVENTION

Figure 1:
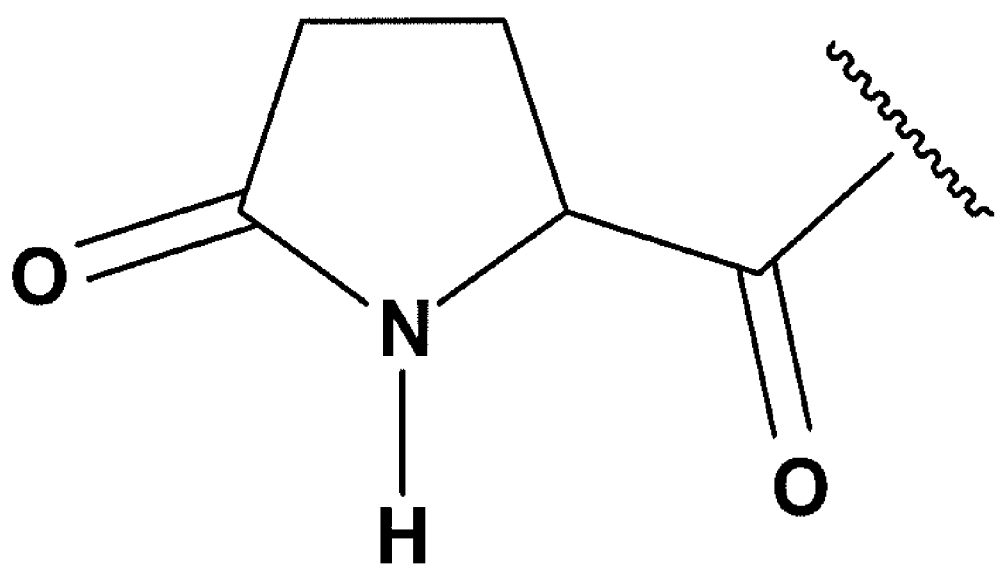
FIG. 1 depicts the structure of pyro-Glu.

Other than a statement about molecular weight and amino acid composition, which are recited in the FDA-approved label for the product, the label and other available literature for COPAXONE® does not provide detailed information about the physiochemical characteristics of the product. It has been previously found that Pyro-Glu (FIG. 1) is a component of Copaxone® (glatiramer acetate or GA) that is present within a predetermined range (U.S. Ser. No. 12/408,058). For example, in many cases the pyro-Glu content of a GA preparation can be between 2000 ppm and 7000 ppm or 2400-6500 ppm.

The production of GA entails polymerization of amino acids to produce a mixture of peptides, referred to as Intermediate-1, followed by partial depolymerization and deprotection of Intermediate-1 to yield Intermediate-2. It has now been found that the level of pyro-Glu in GA can be effectively controlled by controlling the water present during the depolymerization step of the GA manufacturing process, for example, by adjusting the water content at the beginning of and/or during the depolymerization step, e.g., by adding water to a predetermined level at the beginning or during the depolymerization step. Moreover, it has now been found that by properly controlling (e.g., adjusting) the amount of water present during the depolymerization step and the duration of the depolymerization step it is possible to produce GA with a specified pyro-Glu content and a specified peak molecular weight (Mp). In many cases it is specified to have the pyro-Glu content of copolymer or GA be 2000 to 7000 ppm, e.g., 2500-5500 ppm, e.g., 3000-5000 ppm, e.g., 3500-4500 ppm, 2400-6500 ppm, and the water present during the depolymerization reaction or added at the end of the depolymerization reaction is preferably controlled or adjusted to achieve this specified pyro-Glu content. In many cases it is desirable to have the peak molecular weight (Mp) of GA be 5,000 to 9,000 Da, e.g., 6,000 to 8,000 Da, as measured as described in U.S. Pat. No. 7,074,580.

Manufacture of Glatiramer Acetate

Generally, the process for the manufacture of glatiramer acetate includes the following steps:

Step 1: polymerization of N-carboxy anhydrides of L-alanine, benzyl-protected L-glutamic acid, trifluoroacetic acid (TFA) protected L-lysine and L-tyrosine (collectively referred to as NCAs) to result in a protected copolymer (Intermediate-1), Step 2: depolymerization and benzyl deprotection of Intermediate-1 using hydrobromic acid in acetic acid (e.g., phenol treated 33% HBr/acetic acid), and Step 3: deprotection of the TFA-protected lysines on Intermediate-2 (e.g., by treatment with piperidine) to create Intermediate-3, followed by processing to generate GA and further purification and drying of the isolated GA drug substance.

In Step 1 of GA manufacture, the NCAs are co-polymerized in a predetermined ratio using diethylamine as an initiator. Upon consumption of the NCA components, the reaction mixture is quenched in water. The resulting protected polymer (Intermediate-1) is isolated and dried. In Step 2 of GA manufacture, Intermediate-1 is treated with phenol-treated 33% HBr in acetic acid (HBr/AcOH). This results in the cleavage of the benzyl protecting group on the glutamic acids as well as cleavage of peptide bonds throughout the polymer. After a period of time the reaction is quenched with water, and the product polymer is isolated by filtration and washed with water. The product polymer, Intermediate-2, has a reduced molecular weight relative to Intermediate-1. Intermediate-2 is dried before proceeding to Step 3. In Step 3, Intermediate-2 is treated with aqueous piperidine to remove the trifluoroacetyl group on the lysines. The resulting copolymer, Intermediate-3, is subsequently purified using diafiltration/ultrafiltration and the resulting acetate salt is dried to produce Glatiramer Acetate drug substance.

Methods for the manufacture of GA are described in the following publications: U.S. Pat. No. 3,849,550; WO 95/031990 and US 2007-0021324.

Control of Pyro-Glu and Depolymerization with Water

As shown below, GA with a pyro-Glu content of about 4,000 ppm and a peak molecular weight (Mp) about 7,000 Da can prepared by having water present in the depolymerization reaction at about 16% w/w against Intermediate-1. While the amount of water present is expressed here relative to the amount Intermediate 1, the amount of water present can be expressed in any convenient manner, for example: w/w against the weight of Intermediate-1 added to the depolymerization reaction; w/w against the weight of phenol used to treat the HBr/acetic acid added to depolymerization reaction; w/w against the total weight of HBr/acetic acid added to depolymerization reaction; v/v against the total volume of HBr/acetic acid added to the depolymerization reaction; or w/w against the total weight of the depolymerization reaction. Thus, the amount of water present relative to HBr/AcOH on a v/v basis can be calculated from the amount of water present relative to Intermediate-1 on a w/w basis as follows:

$$Vol_{(water)}/Vol_{(HBr/AcOH)} = (Wt_{(water)}/Wt_{(Intermediate-1)}) \times (Wt_{(Intermediate-1)}/Wt_{(HBr/AcOH)}) \times (Wt_{(HBr/AcOH)}/Vol_{(HBr/AcOH)}) \times (Vol_{(water)}/Wt_{(water)}) = (Wt_{(water)}/Wt_{(Intermediate-1)}) \times (Wt_{(Intermediate-1)}/Wt_{(HBr/AcOH)}) \times (Density_{(HBr/AcOH)}/Density_{(water)})$$

The water present during the depolymerization reaction can include water present in the Intermediate-1 added to the depolymerization reaction (e.g., by using Intermediate-1 that is not fully dried) and/or water that is added at the beginning or during the depolymerization reaction. Thus, the amount of water present during at least a portion of the depolymerization reaction can be controlled by adding water to the reaction to achieve a predetermined level of water or by having a certain amount of water present in the Intermediate-1 added to the reaction or by a combination of adding water and having water present in the Intermediate-1. Thus, the amount of water present can be controlled by simply having a reasonably consistent amount of water present in the Intermediate-1. Water can be added to the depolymerization reaction at any time, but is most often present at a predetermined level, e.g., 4-25%, 5-25%, 10-20%, 4-20%, 4-16%, 7-15%, 8-14%, 9-13%, 10-12%, 13-19%, 14-18%, 15-17%, or 16% w/w against the weight of Intermediate-1, at the beginning of the depolymerization reaction. Because the depolymerization reaction can both consume and produce water, the amount of water present can change slightly over the course of the depolymerization reaction.

The amount of water present during the depolymerization step can impact the pyro-Glu content and molecular weight of the resulting GA, as shown by the experiments described below. However, the amount of water present during the depolymerization step can vary over a reasonable range and still be compatible with the production of GA having a desirable pyro-Glu content and molecular weight.

EXAMPLES

Example 1

Figure 2:
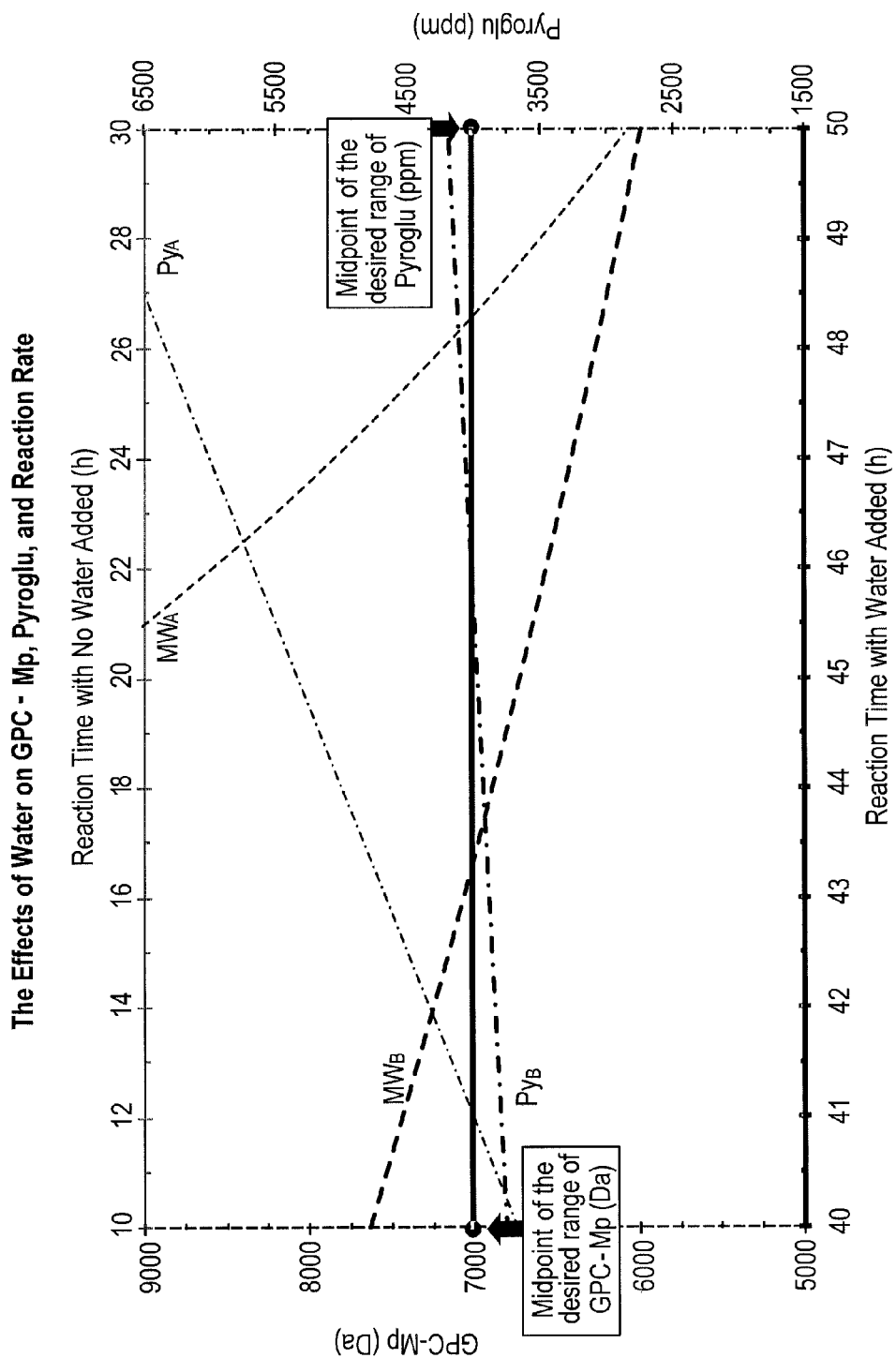
FIG. 2 is a graph depicting the results of studies on the effect of the presence water in the depolymerization reaction used in glatiramer acetate production.

The effect of water present during the depolymerization step, Step 2, on the pyro-Glu content and molecular weight of the resulting GA was examined as follows. Intermediate-1 was produced as described above and divided between two depolymerization reactions (A and B). For Depolymerization reaction A, no water was added. For Depolymerization reaction B, water was added to 16% measured w/w against Intermediate-1. Depolymerization was allowed to proceed at 20° C. Aliquots removed periodically from each reaction were quenched with water and further processed to produce GA. The pyro-Glu content (ppm), measured as described below, and peak molecular weight (Mp) of each of the resulting GA samples were measured. The results of this analysis are shown in FIG. 2. The molecular weight (Mp) scale (Da) is on the left axis, the pyro-Glu concentration scale (ppm) is on the right axis. The time of Depolymerization reaction A (no added water) is on the upper horizontal axis, and the time of Depolymerization reaction B (water present at 16% w/w against intermediate-1) is on the lower horizontal axis. The scale of the graph is such that the horizontal line labeled "Midpoint of desired range of GPC-Mp (Da)/Midpoint of the desired range of pyroGlu (ppm)" indicates both one desirable Mp molecular weight (7,000 Da) and one desirable pyro-Glu concentration for GA (4,000 ppm). The lines labeled $MW_A$ and $MW_B$ depict the Mp molecular weight of the GA produced from material removed from Depolymerization reaction A and Depolymerization reaction B, respectively, at various time points. The lines labeled $Py_A$ and $Py_B$ depict the concentration pyro-Glu in the GA produced from material removed from Depolymerization reaction A and Depolymerization reaction B, respectively, at various time points.

In the absence of added water, the desired combination of molecular weight and pyro-Glu concentration is not achieved. As can be seen in FIG. 2, after about 12 hours (scale on upper horizontal axis) Depolymerization reaction A (no added water) produces material that yields GA having a desired pyro-Glu concentration (about 4,000 ppm), but the molecular weight (Mp) of the GA is about 7,400 Da, above the desired 7,000 Da. As can be also seen in FIG. 2, after about 26 hours (scale on upper horizontal axis) Depolymerization reaction A (no added water) produces material that yields GA having a desired Mp (about 7,000 Da), but the pyro-Glu concentration of the GA is greater than 6,000 ppm, which is above 4,000 ppm (the midpoint of the desired range). In contrast, when water is added to the depolymerization reaction to 16% (w/w against Intermediate-1), the desired combination of molecular weight and pyro-Glu concentration is achieved. As can also be seen from FIG. 2, after about 43 hours Depolymerization reaction B (16% water w/w against Intermediate-1) produces material that yields GA having a desired molecular weight (Mp about 7,000 Da) and a desired pyro-Glu concentration (about 4,000 ppm).

Example 2

In the study described above pyro-Glu concentration of GA was measured as follows. N-terminal pyro-Glu residues were cleaved using *Pyrococcus furiosus* pyro-glutamate aminopeptidase. Pyro-Glu in the resulting enzymatic hydrolysate is isolated by reverse phase liquid chromatography followed by detection at 200 nm using a reference standard curve prepared with known concentrations of L-Pyro-glutamate. Neurotensin (a commercially available polypeptide having 100% pyro-glutamate at the N-terminus) is assayed as a control to ensure the acceptability of the digestion and adequacy of the HPLC separation. The chromatographic analysis is performed using a Waters Atlantis C18 HPLC column and an isocratic mobile phase consisting of 100% Water, adjusted to pH 2.1 with phosphoric acid. Samples and Standards are held at 2-8° C. The peak corresponding to the pyro-glutamate moiety elutes at a retention time of approximately 12 minutes. The direct measure of pyro-glutamate content is on a w/w basis and the results are expressed as ppm (microgram/gram).

What is claimed is:

1. A method for preparing a composition comprising purified glatiramer acetate having a pyroglutamate concentration of 2000-7000 ppm and a Mp of 5000-9000 Da, the method comprising:
   polymerizing N-carboxy anhydrides of L-alanine, benzyl-protected L-glutamic acid, trifluoroacetic acid protected L-lysine and L-tyrosine to generate a sample comprising intermediate-1;
   treating the sample comprising intermediate-1 to partially depolymerize and deprotect benzyl-protected L-glutamic acid, thereby generating a sample comprising intermediate-2, wherein water is present for at least a portion of the treatment in a range of 4-25% weight/weight (w/w) against intermediate-1 present at the beginning of treatment;
   treating the sample comprising intermediate-2 to deprotect trifluoroacetic acid protected L-lysine, thereby generating intermediate-3;
   further processing the intermediate-3 to generate glatiramer acetate; and
   purifying the glatiramer acetate to generate purified glatiramer acetate having a pyroglutamate concentration of 2000-7000 ppm and a Mp of 5000-9000 Da.

2. The method of claim 1, comprising controlling the water present during the at least a portion of the treatment of intermediate-1.

3. The method of claim 2, wherein controlling the water present during the at least a portion of the treatment of intermediate-1 comprises adding water prior to the beginning of the treatment.

4. The method of claim 2, wherein controlling the water present during the at least a portion of the treatment of intermediate-1 comprises adding water during the treatment.

5. The method of claim 1, wherein the water present is in a range selected from the group consisting of 5-25%, 13-19%, and 14-18% w/w against intermediate-1 present at the beginning of treatment.

6. The method of claim 1, wherein the water present is present at 11.2% w/w against intermediate-1 present at the beginning of treatment.

7. The method of claim 1, wherein treatment of intermediate-1 comprises depolymerizing the protected copolymer for 16-64 hours at 17-35° C.

8. The method of claim 7, comprising depolymerizing the protected copolymer for 25-55 hours at 17-35° C.

9. The method of claim 7, comprising depolymerizing the protected copolymer for at least 25 hours at 17-35° C.

10. The method of claim 7, comprising depolymerizing the protected copolymer for 16-64 hours at 18-30° C.

11. The method of claim 7, comprising depolymerizing the protected copolymer for 43-47 hours at 18-22° C.

12. The method of claim 1, wherein treatment of intermediate-1 comprises depolymerizing intermediate-1 using a solution comprising hydrogen bromide and acetic acid.

13. The method of claim 12, wherein treatment of intermediate-1 comprises depolymerizing intermediate-1 using a solution comprising phenol and hydrogen bromide and acetic acid.

14. The method of claim 1, wherein N-carboxy anhydrides of L-alanine, benzyl-protected L-glutamic acid, trifluoroacetic acid protected L-lysine and L-tyrosine are polymerized in predetermined ratios to generate intermediate-1 using diethylamine as an initiator.

15. The method of claim 1, wherein treating the sample comprising intermediate-2 to deprotect trifluoroacetic acid protected L-lysine comprises contacting intermediate-2 with aqueous piperidine.

16. The method of claim 1, wherein the concentration of pyroglutamate in the purified glatiramer acetate is 2500-5500 ppm.

17. The method of claim 1, wherein the Mp of the purified glatiramer acetate is 6500-7500 Da.

18. The method of claim 1, further comprising preparing a pharmaceutical composition comprising at least a portion of the purified glatiramer acetate.

19. The method of claim 1, wherein the concentration of pyroglutamate in the purified glatiramer acetate is 3000-5000 ppm.

20. The method of claim 1 wherein the concentration of pyroglutamate in the purified glatiramer acetate is 3500-4500 ppm.

* * * * *